United States Patent [19]

Lee

[11] Patent Number: 5,248,832
[45] Date of Patent: Sep. 28, 1993

[54] CHEMICAL PROCESS FOR THE MANUFACTURE OF TRIFLUOROACETALDEHYDE HYDRATE OR TRIFLUOROACETALDEHYDE HEMIACETAL

[75] Inventor: Stanley A. Lee, Macclesfield, England

[73] Assignee: Imperial Chemical Industries PLC, London, England

[21] Appl. No.: 886,116

[22] Filed: May 20, 1992

[30] Foreign Application Priority Data

May 21, 1991 [GB] United Kingdom ............... 9110962

[51] Int. Cl.⁵ .................... C07C 45/41; C07C 45/00
[52] U.S. Cl. .................................... 568/495; 568/490
[58] Field of Search ............... 568/448, 449, 490, 495, 568/426; 560/490

[56] References Cited

U.S. PATENT DOCUMENTS

| | | | |
|---|---|---|---|
| 2,568,500 | 9/1951 | Husted et al. | 568/495 |
| 2,852,569 | 9/1958 | Braid et al. | 568/495 |
| 4,211,727 | 7/1980 | Entwistle et al. | 568/490 |
| 4,579,976 | 4/1984 | Cheminal et al. | 568/490 |

FOREIGN PATENT DOCUMENTS

| | | |
|---|---|---|
| 0149905 | 7/1985 | European Pat. Off. . |
| 0156470 | 10/1985 | European Pat. Off. . |
| 1213558 | 11/1970 | United Kingdom . |
| 2140411 | 11/1984 | United Kingdom . |

OTHER PUBLICATIONS

Hill et al., "Reprint from J. Organic Chemistry" vol. 32, Aug. 1967 pp. 2595–2600.
M. Braid, et al., "An Improved Synthesis of Perfluoroaldehydes" *J. Amer. Chem. Soc.* (1954) 76, 4027.
O. R. Pierce, et al., "A New Synthesis of Perfluoroaldehydes" *J. Amer. Chem. Soc.* (1954) 76, 300.
A. Thenappan, et al., "Reduction–Olefination of Esters: A New and Efficient Synthesis of a–Fluoro a,B–Unsaturated Esters" *J. Org. Chem.* (1990) 55, 4639–4642.
D. R. Husted, et al., "The Chemistry of the Perfluoro Acids and Their Derivatives. III. The Perfluoro Adlehydes" *J. Amer. Chem. Soc.* (1952) 74, 5422–5426.
*Chemical Abstracts,* (1981) 94, 156316j.

*Primary Examiner*—Werren B. Lone
*Attorney, Agent, or Firm*—Thomas E. Jackson

[57] ABSTRACT

A process for the manufacture of trifluoroacetaldehyde, or a hydrate or hemiacetal thereof, which comprises reduction of an ester of trifluoroacetic acid with a borohydride reducing agent in a hydroxylic solvent to form trifluoroacetaldehyde hydrate or hemiacetal; whereafter if the free aldehyde is required, water or alcohol is removed from the hydrate or hemiacetal respectively using conventional procedures.

11 Claims, No Drawings

CHEMICAL PROCESS FOR THE MANUFACTURE OF TRIFLUOROACETALDEHYDE HYDRATE OR TRIFLUOROACETALDEHYDE HEMIACETAL

This invention concerns a novel chemical process and, more particularly, it concerns a novel chemical process for the manufacture of trifluoroacetaldehyde, or a hydrate or hemiacetal thereof.

Trifluoroacetaldehyde is a gas at ambient temperature. However, it readily forms adducts with hydroxylic solvents, for example a hydrate with water or a hemiacetal with an alcohol such as methanol or ethanol, and is usually stored and sold in the form of an aqueous solution known as fluoral hydrate. It is useful, for example, in the production of a number of pharmaceutically active compounds such as in the preparation of the human leukocyte elastase inhibitors described in European Patent Application, Publication No. 189305.

A number of methods are known for the preparation of trifluoroacetaldehyde or its adducts with hydroxylic solvents. However such methods generally involve reactions that require extreme temperatures and/or special conditions, such as reactions which have to be carried out in the vapour phase, in the presence of toxic reagents, or at very low temperatures under anhydrous conditions.

One method involves the vapour phase fluorination of chloral using hydrogen fluoride, for example as described in European patent application publication number EP 156470. This method can be operated on a manufacturing scale, but the partially fluorinated aldehyde impurities obtained with the reaction product are undesirable in material intended for use in the manufacture of pharmaceuticals.

Another method involves the hydrolysis of $F_3CCHBrCl$ in the presence of concentrated sulphuric acid and mercuric oxide, for example as described in Chemical Abstracts, abstract number CA 94 156316j (abstract of Czechoslovakian patent application publication number CS 183467). This process is unattractive for operation on a commercial scale because the reagents used are hazardous to the environment.

A number of other preparations of trifluoroacetaldehyde have been described in the literature. For example, Pierce and Kane (*J.Amer.Chem.Soc.,* 1954, 76, 300) have described a preparation which involves the reduction of an ester of trifluoroacetic acid with lithium aluminium hydride at $-70°$ C. under anhydrous conditions. More recently, Thenappan and Burton (*J.Org.Chem.,* 1990, 55, 4639) have described a variant of this process which involves the reduction of ethyl trifluoroacetate with diisobutylaluminium hydride (DIBAL) at $-78°$ C. under anhydrous conditions. Unfortunately, the extreme reaction conditions required, and potentially hazardous nature of the reducing agent make these preparations unattractive for operation on a manufacturing scale.

Surprisingly, it has now been discovered that fluoral hydrate can readily be obtained by reacting ethyl trifluoroacetate with sodium borohydride in the presence of water.

According to the invention there is provided a process for the manufacture of trifluoroacetaldehyde, or a hydrate or hemiacetal thereof, which comprises reduction of an ester of trifluoroacetic acid with a borohydride reducing agent in a hydroxylic solvent to form trifluoroacetaldehyde hydrate or hemiacetal; whereafter if the free aldehyde is required, water or alcohol is removed from the hydrate or hemiacetal respectively using conventional procedures.

The process according to the invention enjoys a number of advantages; it employs a readily available starting material, it can readily be operated on a large scale, and it affords a product free of other haloacetaldehydes, which is particularily important for material intended to be used to make pharmaceutical products.

A particular ester of trifluoroacetic acid is, for example, an alkyl ester, particularly a (1-6C)alkyl ester, for example a (1-4C)alkyl ester such as a methyl, ethyl or propyl ester. Especially preferred is the ethyl ester.

A particular borohydride reducing agent is, for examples an alkali metal borohydride, such as sodium borohydride, potassium borohydride or lithium borohydride, of which sodium borohydride is preferred.

A particular hydroxylic solvent is, for example, water, a lower alcohol (such as methanol or ethanol) or a mixture thereof, optionally in combination with an inert organic solvent or diluent for example, an ether (such as tetrahydrofuran, dioxane, methyl tert-butyl ether, 2-methoxyethyl ether (also called diglyme and diethylene glycol dimethyl ether) or dimethoxyethane). It will be appreciated that if vater, or a mixture of water and an inert organic solvent, is used as solvent, the product obtained is a hydrate of trifluoroacetaldehyde. Similarly, if an alcohol (or an alcohol together with an inert organic solvent) is used as solvent, the product is mainly in the form of a hemiacetal of trifluoroacetaldehyde. If a mixture of water and an alcohol is used as solvent (with or without an inert organic solvent) then the product may be present as both a hydrate and a hemiacetal. A particularly preferred hydroxylic solvent is, for example, a mixture of water and an ether, especially tetrahydrofuran or 2-methoxyethyl ether.

The reaction is generally carried out at a temperature in the range, for example, $-10°$ C. to $50°$ C., and preferably in the range $-10°$ to $40°$ C. (such as from $0°$ to $40°$ C.), and more preferably in the range $-10°$ C. to $30°$ C. (such as from $10°$ to $30°$ C.), especially from $-10°$ to $20°$ C. (such as from $-10°$ to $10°$ C.). The trifluoroacetaldehyde hydrate or hemiacetal formed may conveniently be isolated using standard work-up procedures and purified by procedures well known in the art, for example by fractional distillation.

It will be appreciated that, dependent on the solvent or solvents employed in the reaction, purification by fractional distillation may result in some of the solvent or solvents co-distilling with the product of the reaction. Consequently the fractional distillation procedure may need to be repeated, or an alternative purification procedure employed if pure product free from solvent is required. For example, if pure trifluoroacetaldehyde hydrate is required, the purification procedure described by Husted and Ahlbrecht (*J. Amer. Chem. Soc.,* 1952, 74, 5422-5426) may be carried out.

Although an excess of the borohydride reducing agent may be used in the process of the invention, for example about 2 or 3 equivalents, it is generally preferred to use about one equivalent of the borohydride reducing agent, for example, about one equivalent of sodium borohydride. Accordingly, from 1 to 3 equivalents of borohydride reducing agent are preferably used. It will be appreciated that the use of one equivalent of sodium borohydride corresponds with the use of one quarter of a mole of sodium borohydride per mole of ester.

Preferably the borohydride reducing agent is added stepwise to the ester of trifluoroacetic acid. Conveniently it is added as a solution in one or more of the components of the hydroxylic solvent. For example, an alkali metal borohydride (such as sodium borohydride) is preferably added to the ester as a solution in water when trifluoroacetaldehyde hydrate is required.

The esters of trifluoroacetic acid are commercially available or known, or they can be made by analogy therewith using conventional procedures of organic chemistry.

The process of the invention is particularly suitable for obtaining trifluoroacetaldehyde hydrate.

The use of a borohydride to reduce an ester to an aldehyde is surprising. It is well known in the art, for example as described in standard textbooks of organic chemistry such as Practical Organic Chemistry edited by Vogel, page 341, that carboxyalkyl groups in general do not undergo reduction with potassium or sodium borohydrides. By contrast, aldehydes and their hydrates, are reduced with alkali metal borohydrides to the corresponding alcohols. In particular, trichloroacetaldehyde (chloral) is known to be reduced as its hydrate to 2,2,2-trichloroethanol with potassium borohydride even under mild conditions, for example at 20°-30° C. in water.

The invention will now be illustrated by the following Examples.

EXAMPLE 1

A solution of sodium borohydride (11.5 g) in water (100 ml) was added over a period of one hour to a solution of ethyl trifluoroacetate (142 g) in tetrahydrofuran (THF) (500 ml) maintaining the temperature of the reaction mixture between 15° and 18° C. When the addition was complete, water (10 ml) was added and the mixture was stirred for a further 30 minutes. Concentrated hydrochloric acid (10 ml) was then added dropwise with stirring to adjust the mixture to pH 2-3, followed by solid sodium chloride (15 g). The organic phase was separated and fractionally distilled at atmospheric pressure to give trifluoroacetaldehyde hydrate (36 g) as a 60% w/w aqueous solution; b.p. 104°-105° C.

Pure trifluoroacetaldehyde or its hydrate may subsequently be obtained using a similar procedure to that described in *J. Amer. Chem. Soc.*, 1952, 74, 5422-5426.

EXAMPLE 2

A solution of sodium borohydride (15.05 g) in water (37.5 ml) was added slowly to a solution of ethyl trifluoroacetate (250 g) in 2-methoxyethyl ether (500 ml) with stirring, keeping the temperature below 0° C. After all of the sodium borohydride solution had been added, the reaction mixture was stirred for a further half of an hour, and then the mixture was analysed by gas-liquid chromatography. This revealed that the reaction was incomplete. More sodium borohydride (1.51 g) in water (4 ml) was then added with stirring, keeping the temperature between −5° and 0° C., and then the stirring was continued for a further half of an hour. The reaction mixture was then analysed again by gas-liquid chromatography, whereafter the addition of further sodium borohydride (1.51 g) was also repeated. The reaction mixture was then stirred for a further hour, and then a solution of concentrated sulphuric acid (2.4 ml) in water (12 ml) was added, and the solid residue was filtered off. The remaining solution was then fractionally distilled at atmospheric pressure. A fraction taken over the boiling range 100° to 105° C. contained 155.6 g of fluoral hydrate in water. NMR analysis of this fraction indicated a yield of 58%, based upon ethyl trifluoroacetate.

What is claimed is:

1. A process for the manufacture of trifluoroacetaldehyde hydrate or a trifluoroacetaldehyde hemiacetal, which comprises reduction of a (1-6C)alkyl ester of trifluoroacetic acid with up to 3 equivalents of an alkali metal borohydride, in a hydroxylic solvent which comprises water, a lower alcohol or a mixture thereof, at a temperature of up to 30° C.

2. A process as claimed in claim 1, in which the alkali metal borohydride is sodium borohydride.

3. A process as claimed in claim 1 or claim 2, in which the (1-6C)alkyl ester is a methyl, ethyl or propyl ester.

4. A process as claimed in a claim 1 or claim 2, in which the lower alcohol is methanol or ethanol.

5. A process as claimed in claim 1 or claim 2, in which the hydroxylic solvent is a mixture of water and an ether.

6. A process as claimed in claim 5, in which the ether is tetrahydrofuran or 2-methoxyethyl ether.

7. A process as claimed in claim 1 or claim 2, in which the reaction temperature is in the range of from −10° to 10° C.

8. A process as claimed in claim 1 or claim 2, in which the alkali metal borohydride is added slowly to the ester of trifluoroacetic acid as a solution in water.

9. A process as claimed in claim 1 or claim 2, in which from 1 to 2 equivalents of borohydride are used.

10. A process as claimed in claim 9, in which about one equivalent of borohydride is used.

11. A process for the manufacture of trifluoroacetaldehyde hydrate, which comprises reduction of a (1-4C)alkyl ester of trifluoroacetic acid with about one equivalent of sodium borohydride in a hydroxylic solvent which comprises water at a temperature in the range of from −10° to 10° C.

* * * * *